(12) United States Patent
Cichocki, Jr.

(10) Patent No.: US 7,481,826 B2
(45) Date of Patent: Jan. 27, 2009

(54) FLUID EMITTING SUTURE NEEDLE

(75) Inventor: Frank Richard Cichocki, Jr., Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 528 days.

(21) Appl. No.: 10/674,332

(22) Filed: Sep. 30, 2003

(65) Prior Publication Data
US 2005/0070959 A1 Mar. 31, 2005

(51) Int. Cl.
*A61B 17/06* (2006.01)
*A61M 37/00* (2006.01)
*A61M 5/32* (2006.01)

(52) U.S. Cl. .......... 606/224; 604/148; 604/272; 606/222

(58) Field of Classification Search .......... 604/890.1, 604/140, 148, 141, 93.01, 272–274, 264, 604/187, 181, 3, 411; 606/222, 223
See application file for complete search history.

(56) References Cited

U.S. PATENT DOCUMENTS

| | | | |
|---|---|---|---|
| 3,308,820 A * | 3/1967 | Hubbard | 604/148 |
| 3,918,455 A | 11/1975 | Coplan | |
| 4,805,292 A | 2/1989 | Noguchi | |
| 4,901,722 A | 2/1990 | Noguchi | |
| 4,932,962 A | 6/1990 | Yoon et al. | |
| 4,955,881 A | 9/1990 | Eckenhoff | |
| 4,981,149 A * | 1/1991 | Yoon et al. | 128/898 |
| 5,053,047 A | 10/1991 | Yoon | |
| 5,066,278 A | 11/1991 | Hirschberg | |
| 5,649,961 A * | 7/1997 | McGregor et al. | 606/222 |
| 5,876,741 A | 3/1999 | Ron | |
| 6,001,090 A | 12/1999 | Lenhart | |
| 6,241,710 B1 | 6/2001 | VanTassel et al. | |
| 6,245,091 B1 | 6/2001 | Buncke | |
| 6,485,462 B1 | 11/2002 | Kriesel | |
| 6,457,769 B2 | 4/2003 | VanTassel et al. | |
| 2002/0065492 A1 | 5/2002 | McCuckin et al. | |
| 2003/0028204 A1 | 2/2003 | Li et al. | |
| 2003/0130626 A1 | 7/2003 | VanTassesl et al. | |

* cited by examiner

*Primary Examiner*—Darwin P Erezo
*Assistant Examiner*—Melissa Ryckman
(74) *Attorney, Agent, or Firm*—Roberts Mlotkowski Safran & Cole, P.C.

(57) ABSTRACT

A multifunctional suture needle that may be used to draw a suture through tissue surrounding a wound while simultaneously delivering a bioactive fluid through the needle tip. The suture needle possesses an internal cavity capable of containing a fluid, and a fine aperture adjacent to the point of the needle through which the fluid may egress. The fluid may be driven from the needle through the needle tip with a compressed gas that is sealed within the cavity adjacent to the fluid. Alternatively a fluid conducting suture may be employed to deliver fluid through the internal passage of the suture needle and out the aperture adjacent to the tip of the needle. The rate at which the fluid is emitted from the suture needle may be controlled by carefully selecting the fluid viscosity, design of the needle or suture passages, and pressure applied to the fluid.

2 Claims, 14 Drawing Sheets

74
Active Needle

75
Control

FLUID EMITTING SUTURE NEEDLE

FIELD OF INVENTION

The present invention relates to multifunctional devices that may be used to close surgical wounds. More particularly the invention relates to functional suture needles that may be used to emit therapeutic or bioactive agents or fluids during the wound closure procedure. In particular, the invention relates to a device that incorporates a suture needle having an internal passage that is in turn connected to a fine orifice adjacent to the needle tip, wherein the fluid is emitted through said orifice.

BACKGROUND OF INVENTION

Suture needles have long been used to guide and draw sutures through the tissue surrounding a wound. Even today, the function of commercially available suture needles continues to be singular in nature, namely to guide and position the suture to close wounds.

Unlike hypodermic needles commonly employed to deliver fluids subcutaneously, suture needles must serve as a tool to guide and draw a suture into position along the path of a wound. Hypodermic needles employ a hollow needle and pressurizable reservoir to deliver fluids to the body. The hypodermic needle is typically hollow through its entire length with a sharp distal end for penetrating tissue and a proximal end that is hermetically sealed to a connector that may be attached to a syringe or IV tube. A syringe or IV is attached directly to the hyperdermic needle to deliver a predetermined quantity of fluid. Although this time-tested method of delivering medication to the body serves its singular purpose effectively, it is not readily adapted to serve the alternate function of closing wounds, since multiple passes of the suture needle through the tissue surrounding the wound and knotting of the suture are typically involved in the wound closure process. Consequently, the large syringe or reservoir employed with hypodermic needles may not be connected directly to the suture needle. Likewise, because suture needles are not designed to transport a fluid and are not easily connected directly to an external reservoir of fluid without severely impairing their primary function as a tool for wound closure, suture needles are not used for drug delivery. Nevertheless, a multifunctional suture needle that satisfies the traditional requirements of wound closure while simultaneously supplying a therapeutic fluid could provide many benefits associated with localized drug delivery to the wound site.

Although suture needles have been improved over the years to exhibit an exemplary combination of handling and performance properties, including but not limited to strength, stiffness, ductility, and lubricity, a number of problems are associated with the use of surgical needles. For example, the transmission of blood born pathogens occurring from accidental needle sticks poses a risk to the medical professionals conducting the wound closure procedure. Suture needles that exhibit a blunt point have been used to reduce the likelihood of an accidental needle stick. This approach relies on the fact that a high force is required to penetrate the skin with a blunt point needle. However, since most tissue is not easily penetrated with blunt point needles, the additional level of safety from accidental needle sticks is achieved only by sacrificing handling characteristics and performance of the needle. Additionally, blunt point needles in many cases will cause a higher level of tissue trauma than their sharp point counterparts. Therefore, a suture needle that affords improved resistance to the transmission of blood borne pathogens while retaining exemplary penetration performance would be beneficial to both surgeon and patient. In particular, a suture needle that emits an antiviral fluid through its tip may provide additional protection by washing blood from the tip and neutralizing virus contained therein.

A suture needle that emits an active fluid may provide benefit to the patient and surgeon in many ways. One example is associated with the need to achieve hemostasis during wound closure. Hemorrhaging often occurs through the holes formed by suture needles. Besides posing a nuisance to the surgeon, in certain surgeries such as those involving blood vessel anastomosis and certain organ surgeries, or in the cases where patients are suffering from hemophilia or consuming blood thinning medicines, hemostasis may be quite difficult to achieve. Specialized suture needles that enable the delivery of hemostatic agents or bioadsorbable sealants during wound closure may provide an opportunity to reduce bleeding through needle holes. Alternatively, vaso-constricting medicines when delivered though the suture needle may afford hemostasis at the wound site itself.

As a further example, surgical site infections are a source of many post-operative complications and deaths each year. Sutures themselves often act as a site for microbial colonization. In an attempt to reduce the rate of surgical site infections, braided sutures coated with antimicrobial agents were commercially developed. Many of these sutures have demonstrated short term efficacy in preventing the colonization of microbes in the proximity of the suture itself. However, the types of sutures that may be effectively combined with antimicrobial agents, as well as the duration and zone of efficacy are limited. Hence a number of benefits over the current antimicrobial suture technologies may be achieved with a suture needle that emits a fluid to the tissue surrounding the wound. In particular, the quantity of antimicrobial agent that may be delivered from a suture needle can be much greater than the quantity of active agent that may be incorporated into commercially available antimicrobial sutures. A larger quantity of antimicrobial agent may extend the duration of efficacy as well as extend the zone over which an antimicrobial effect is realized. Moreover, a combination of antimicrobial agents may be mixed in a single liquid vehicle to help combat a broader flora of microbes.

SUMMARY OF INVENTION

Generally, the invention provides a suture needle containing an internal cavity and an opening at or in the proximity of the distal end of the needle, where the opening allows for the delivery of a fluid during a wound closure procedure. The fluid may be contained in the internal cavity and may be subjected to a pressure that drives the fluid through the opening in a controlled manner.

One embodiment of the invention provides for a suture needle having a internal cavity therein and comprising a proximal end, a distal end, a point on the distal end and an opening at or in the proximity of the distal end; a non-hollow portion at or adjacent to the proximal end; wherein the internal cavity is in fluid communication with said opening at one end and terminates at the non-hollow portion on the other; a fluid residing within the internal cavity; and a compressed gas residing within the internal cavity between the fluid and the non-hollow portion.

Another embodiment provides a suture needle assembly comprising a suture needle having a first internal cavity therein and comprising a proximal end, a distal end, a point on the distal end and an opening at or in the proximity of the distal end; a connector having a second internal cavity therein and comprising a proximal end, a distal end and a non-hollow portion at or in the proximity of the proximal end of the connector; wherein the first internal cavity of the suture needle is in fluid communication with the opening of the suture needle at one end and with the second internal cavity of the connector at the other end, and the second internal cavity terminates at said non-hollow portion of the connector; a fluid residing within the first internal cavity of the suture needle or within the first internal cavity of the suture needle and the second internal cavity of the connector; and a compressed gas residing between the fluid and the non-hollow portion of the connector.

An additional embodiment is directed to a suture needle/suture assembly comprising a suture needle having an internal cavity therein and comprising a proximal end, a distal end, a point on the distal end and an opening at or in the proximity of the distal end; a suture having at least one internal passageway therein and comprising a proximal end, a distal end and a seal at a point located between the proximal and distal ends of the suture; said at least one internal passageway extending along a length of the suture; wherein the internal cavity of the suture needle is in fluid communication with the opening of the suture needle at one end and with the at least one internal passageway of the suture at the other; a fluid residing within the internal cavity of the suture needle or within the internal cavity of the suture needle and the at least one internal passageway of the suture; and a compressed gas residing between the fluid and the seal on the suture.

Another embodiment provides a suture needle/suture assembly comprising a suture needle having an internal cavity therein and comprising a proximal end, a distal end, a point on the distal end and an opening at or in the proximity of the distal end; a suture having at least one internal passageway and comprising a proximal end and a distal end; the at least one internal passageway extending along a length of the suture from the distal end to the proximal end of the suture; wherein said internal cavity of said suture needle is in fluid communication with the opening of the suture needle at one end and with said at least one internal passageway of said suture at the other.

DETAILED DESCRIPTION OF THE INVENTION

A suture needle that can meet the requirements of wound closure while simultaneously serving as a device for the delivery of a therapeutic or bioactive agent or medication may provide many benefits. With such a device, practically any agent or medication that is fluid may be delivered to the tissue in closest contact with the wound, where it is often most needed and most effective. However, while the premise of employing a suture needle with the alternate function of drug delivery is appealing, the form of such a device is not apparent.

As discussed above, fluids are commonly delivered subcutaneously through hollow needles attached to a syringe. In this case, the syringe acts as both a reservoir and pressurizing device for expulsion of the fluid through the needle. Suture needles on the other hand serve a primary role as a tool for wound closure; forging a path and drawing the suture through the tissue surrounding the wound. Consequently, a syringe reservoir may not be attached directly to the suture needle while simultaneously using the needle to close a wound. Moreover, any significant variation of needle design that would lead to the formation of larger needle holes, or any design that would compromise the handling characteristics, performance and function of the suture needle would not be well received by surgeons or patients. Hence, the present invention describes a suture needle that may be used to deliver a fluid during wound closure without deviating from the traditional design and functional requirements of a suture needle.

Figure 1:
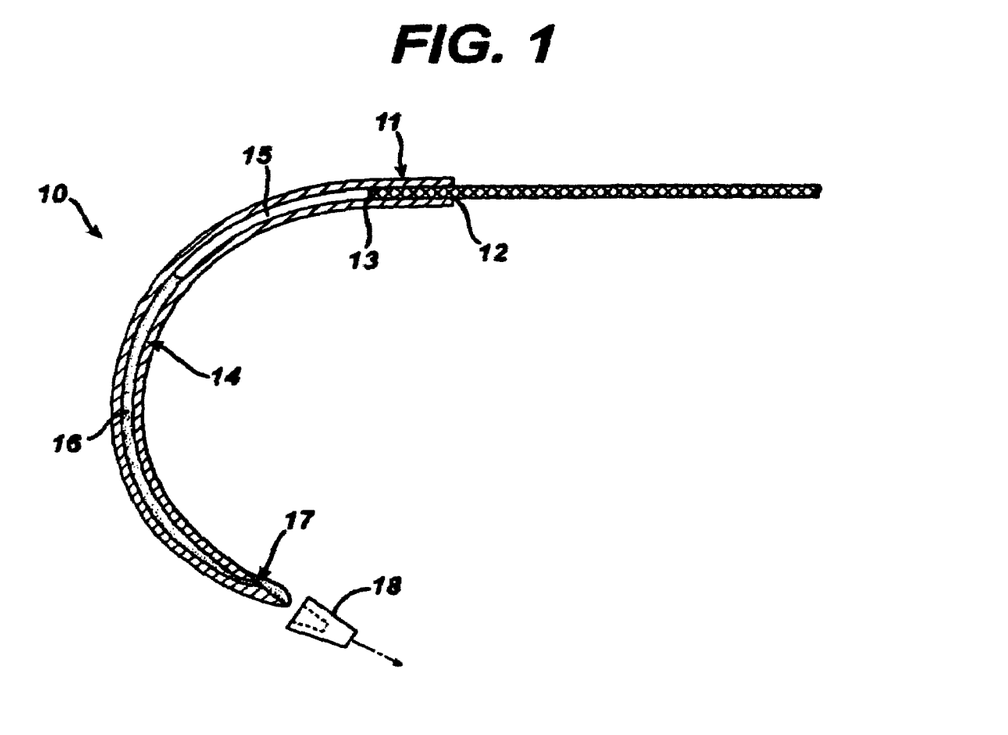
FIG. 1 is a schematic cross-sectional view of a fluid emitting suture needle.

A cross-sectional view of one embodiment of the invention is shown in FIG. 1. Specifically, a curved suture needle 10 that is capable of containing and emitting a fluid through an opening 17 at or adjacent to the distal end of a needle is shown. The suture needle 10 has a proximal end 11 for suture attachment that may be in the form of a hole 12 or channel, a gas tight seal 13, a internal cavity 14 that contains a compressed gas 15 adjacent to the therapeutic or bioactive agent or medication 16 to be delivered, an opening 17 at or in proximity of the distal end of the suture needle and a cap or stopper 18 that seals the opening and contains the fluid within the internal cavity 14. When cap or stopper 18 is removed, the therapeutic or bioactive agent or medication 16 is driven out through opening 17 by the compressed gas 15 contained in the internal cavity 14.

Figure 2A:
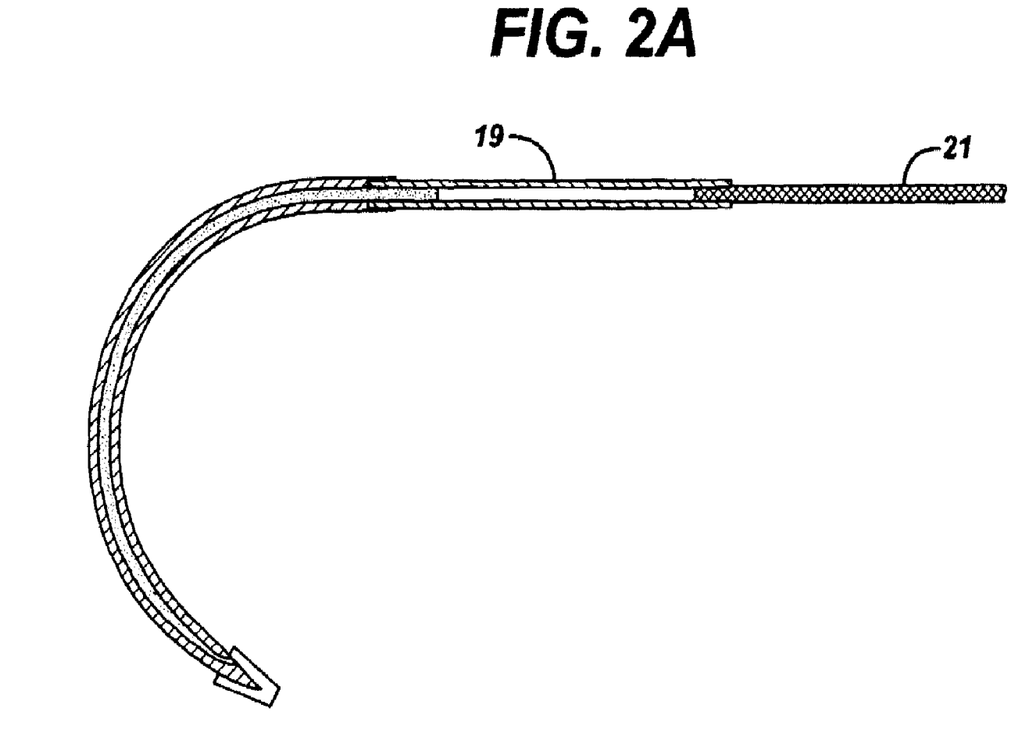
FIGS. 2A, 2B, 2C and 2D schematically illustrate various embodiments of the suture needle/suture assembly of the invention.
Figure 2B:
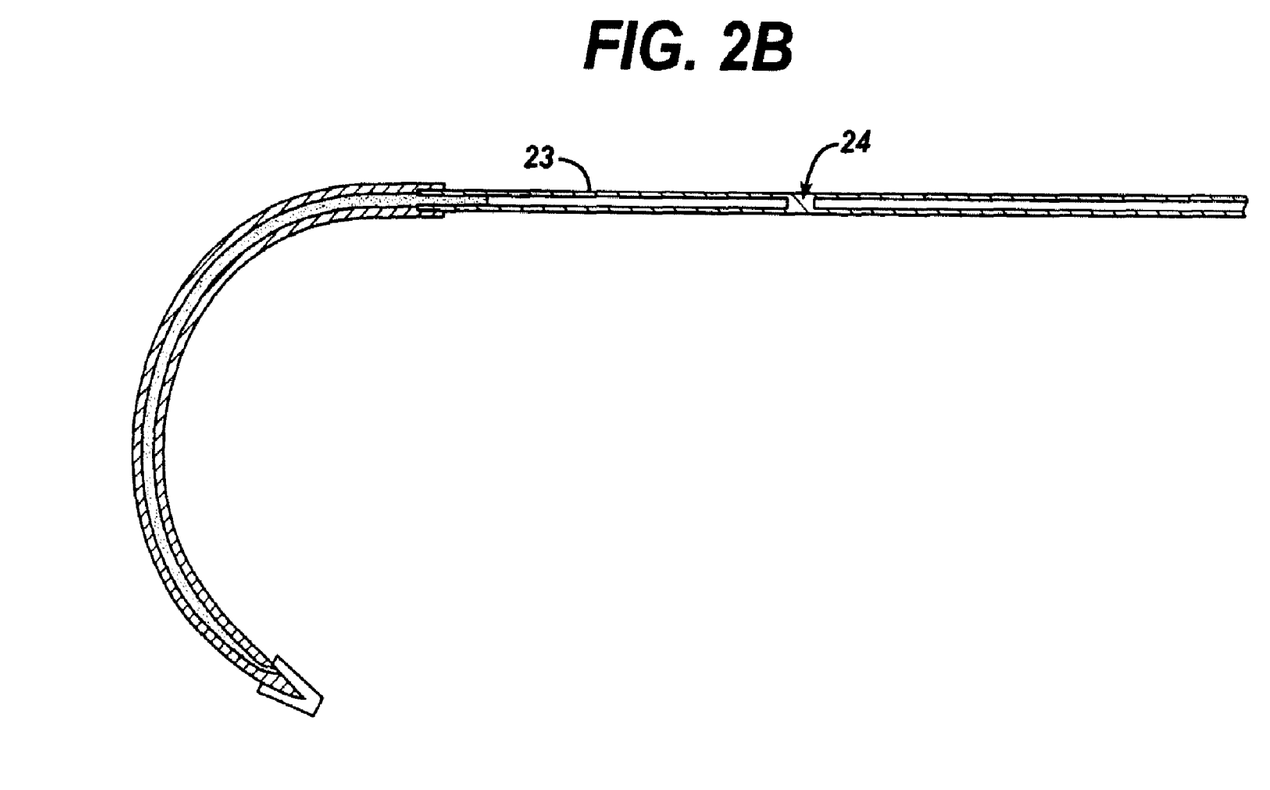
Figure 2C:
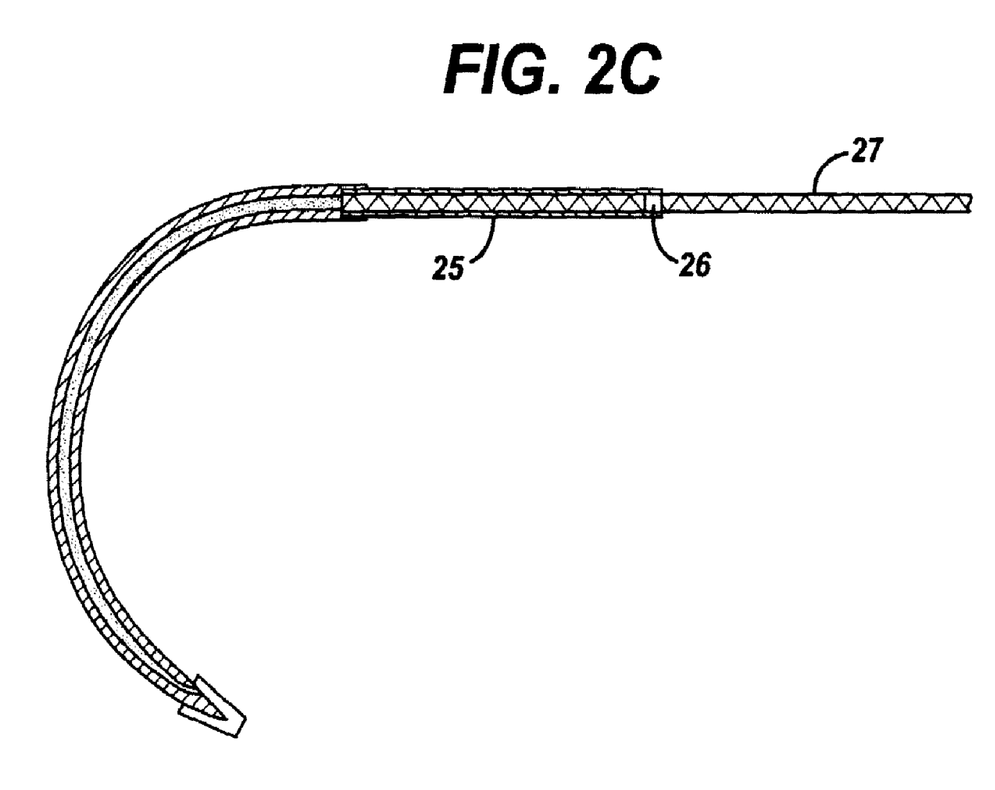
Figure 2D:
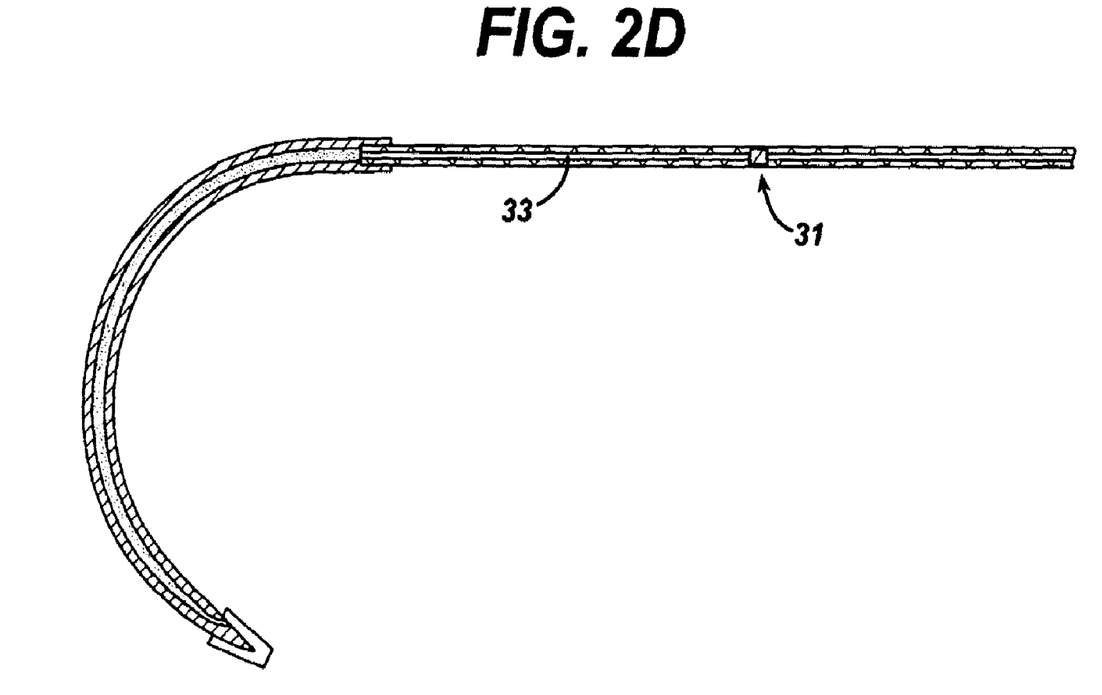

Additional embodiments of the suture needle are described herein. For example, in certain applications it may be desirable to deliver a larger quantity of fluid than may be contained within the internal cavity of the suture needle shown in FIG. 1. If only an incremental increase in fluid volume is required, the internal cavity may be extended by use of a connector 19 as shown in FIG. 2A. In this embodiment, the internal cavity of the suture needle is in direct contact with the internal cavity of the connector 19, in essence increasing the volume of fluid that may be contained within the internal cavity. A suture 21 may be attached to the proximal end of the connector in any conventional manner and sealed to make the internal cavity gas tight. Variations of this embodiment include, but are not limited to, connecting the internal cavity of the suture needle to a hollow monofilament suture 23 that contains a gas tight seal 24 some distance proximal to the proximal end of the suture needle, as shown in FIG. 2B. Alternatively, a braided suture or a multifilament non-braided tow 27 may be coated with a thin polymeric layer 25 and sealed 26 some distance proximal to the proximal end of the suture needle, where the interstices between the multiple filaments of the braid or tow 27 would then act as a cavity, in conjunction with the internal cavity of the suture needle, to contain fluid and compressed gas, as shown in FIG. 2C. In an alternate embodiment, a small tube 33 may be partially or completely woven into a braided suture or a multifilament tow with one end of the lumen being connected to the internal cavity of the suture needle at one end and sealed on the other end 31, as shown in FIG. 2D. All of the aforementioned embodiments for containing and delivering a fluid through a suture needle would permit the surgeon to use an interrupted or continuous stitch in a wound closure procedure.

Figure 3:
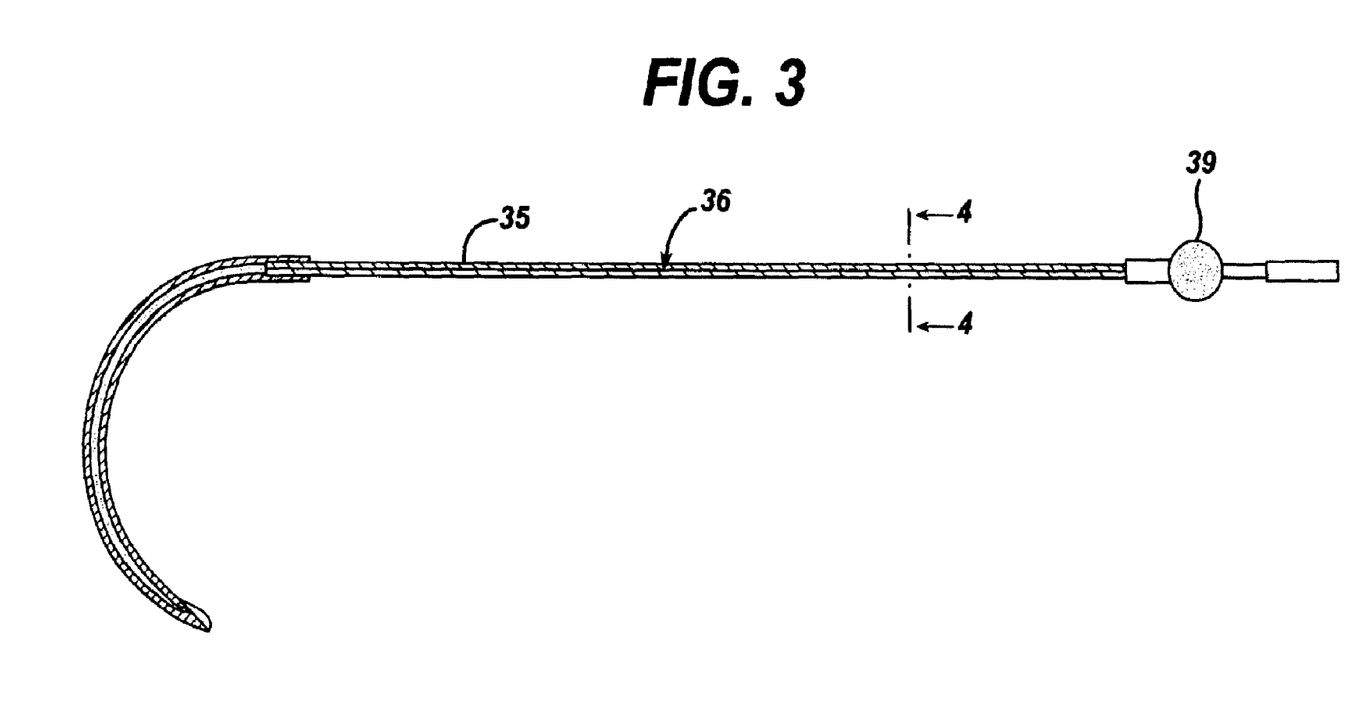
FIG. 3 is a schematic cross-sectional view of an embodiment of the suture needle/suture assembly of the invention.
Figure 4A:
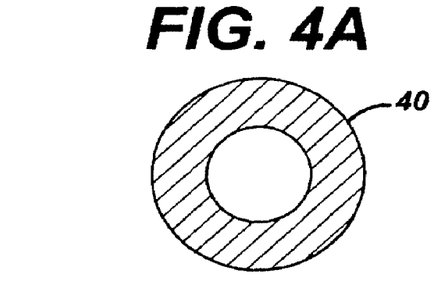
FIGS. 4A, 4B, 4C and 4D are schematic cross-sectional views of the suture shown in FIG. 3 taken along the 4-4 plane.
Figure 4B:
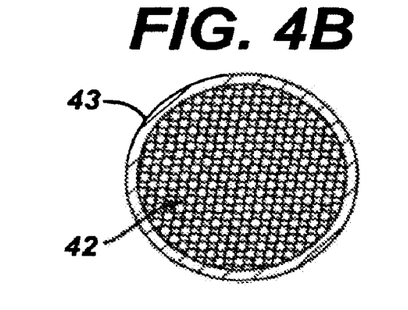
Figure 4C:
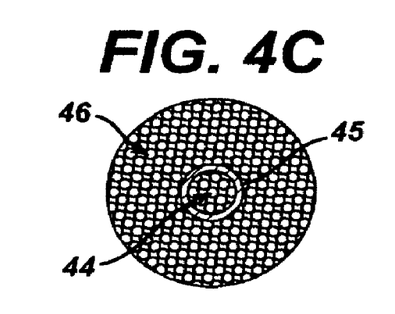
Figure 4D:
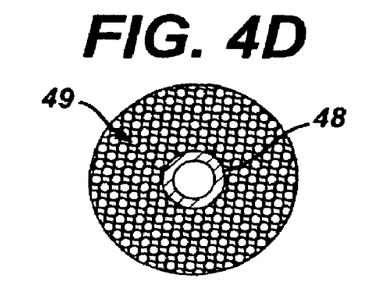

An even larger increase in fluid volume may be achieved by connecting the suture needle to a suture 35 that in turn contains at least one internal passageway 36 capable of conducting a fluid under pressure as shown in FIG. 3. One end of the fluid conducting suture may be connected to the internal cavity of the suture needle and the other end to a reservoir 39 that will supply a pressure to drive the fluid through the suture and out the suture needle. A variety of fluid conducting sutures may be employed. In the simplest embodiment, a hollow monofilament suture 40 as shown in FIG. 4A may be used to conduct the fluid from a reservoir to the suture needle as shown in FIG. 4A. Alternatively, a braided suture 42 or multifilament non-braided tow that has been coated with a thin polymeric layer 43 as shown in FIG. 4B may be used, or a braided suture 44 or multifilament tow coated with a polymer 45 contained within a larger braided suture 46 or multifilament tow, where the interstices between the multiple filaments of the internal braid or tow would then act as conduits to transport fluid as shown in FIG. 4C may be used. In an additional embodiment, a small tube 48 may be woven into a braided suture 49 or multifilament tow as shown in FIG. 4D and used to conduct a fluid from the reservoir.

Figure 5A:
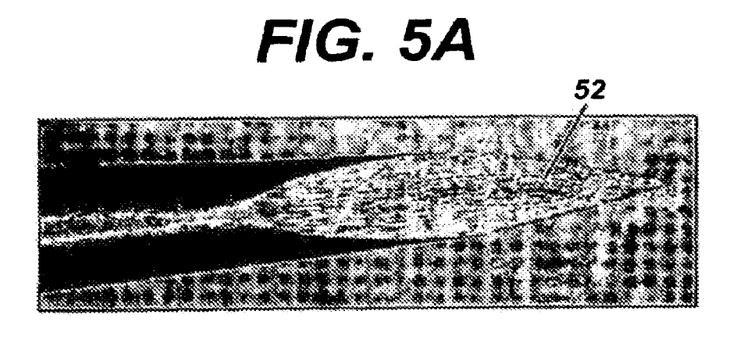
FIGS. 5A, 5B and 5C are photomicrographs of the tips of fluid emitting suture needles.
Figure 5B:
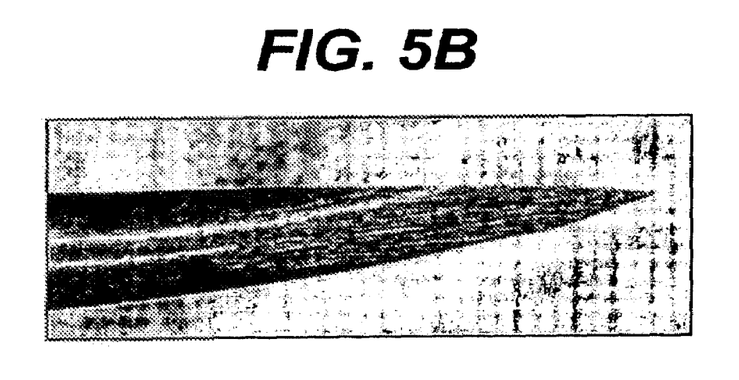
Figure 5C:
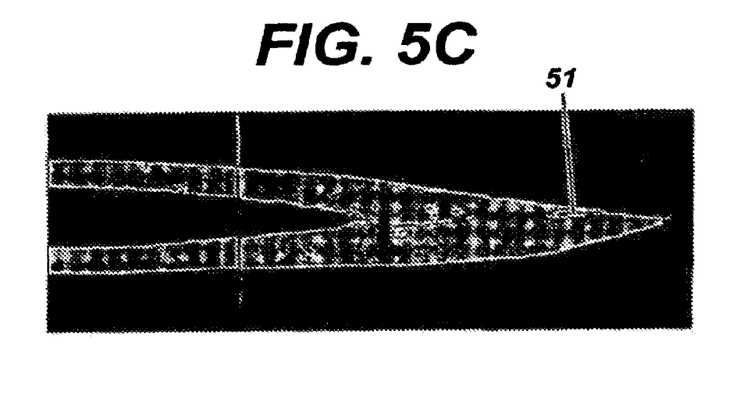

The distal end of the suture needle described in this invention serves two vital purposes. Firstly, it must effectively penetrate tissue at a performance level similar to that attainable with commercially available suture needles. Secondly, it must serve as a site for egress of the therapeutic or bioactive agent or fluid. The design of modern suture needle tips reflects many generations of refinement. It is therefore desirable to use these same needle tip designs with the suture needle of the invention. An image of a fluid emitting suture needle with a needle tip design commonly referred to as taper cutting is shown in top and side views in FIGS. 5A and 5B respectively. A cross-section view of a mounted and polished needle is shown in FIG. 5C. As seen in FIG. 5C, the internal cavity of the needle may taper down to a fine opening 51 that extends to a position adjacent to the top flat surface of the needle tip.

The cap or stopper at the distal end of the suture needle shown in FIGS. 1, 2A, 2B, 2C and 2D may be made from any material that exhibits sufficient elasticity to make a fluid-tight seal between the needle body and cap. Polymeric materials, and more specifically elastomeric polymers, including but not limited to flexible polyvinyl chloride, polyurethanes, polyethylenes, and silicone rubbers, are well suited to this application. The cap or stopper may be in the form of a tube, sealed at one end and open on the other, that slides over the needle tip, or it may be in the form of a solid cork. In this latter embodiment, the needle tip would be forced into the cork to cover the aperture located at the needle tip.

Figure 6A:
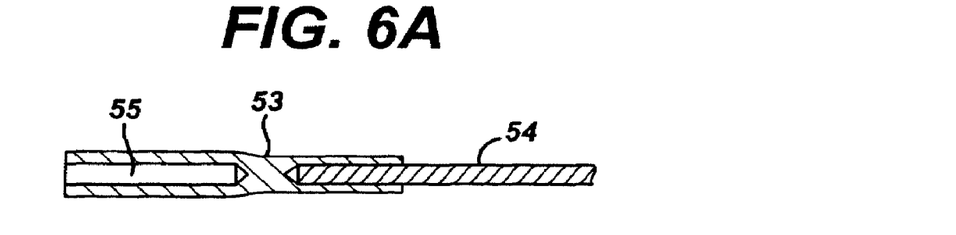
FIGS. 6A, 6B, 6C and 6D are schematic cross-sectional views of the proximal end of the suture needle of FIG. 1.
Figure 6B:
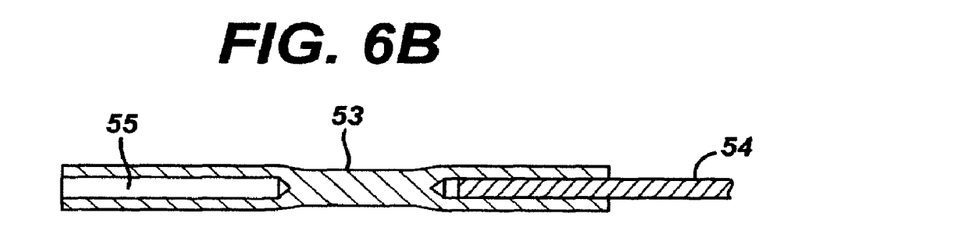
Figure 6C:
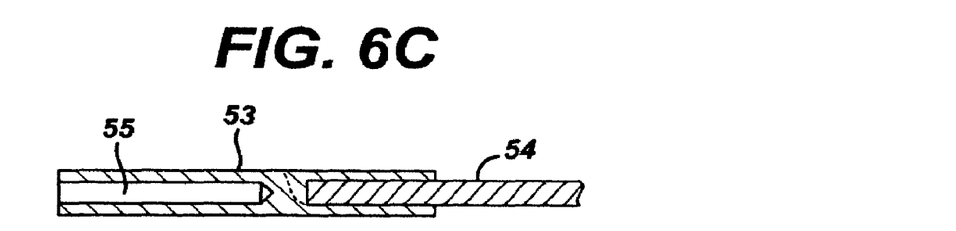
Figure 6D:
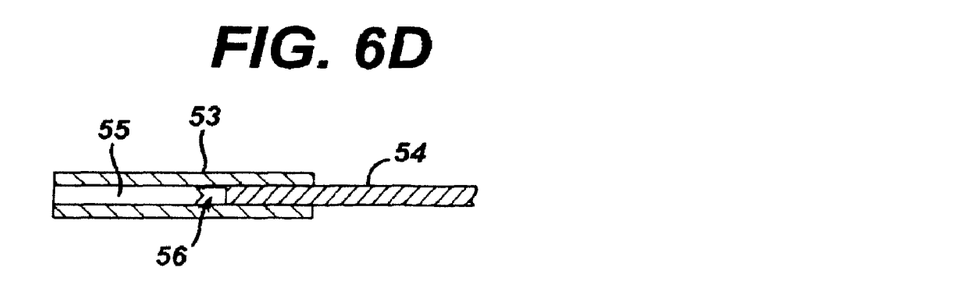

The seal 13 at the proximal end of the suture needle shown in FIG. 1 may be formed in a variety of ways. However, in order to contain a gas under pressure for an extended period of time, for the embodiment described in FIG. 1, the seal should exhibit resistance to gas diffusion. The seal between the suture 54 and the internal cavity 55 may be made by collapsing the metal tube 53 in a swaging operation as shown in FIGS. 6A and 6B or in a channel forming operation as shown in FIG. 6C, each of which are commonly employed in the manufacture of suture needles. A combination of swaging and channel forming operations may also be employed. Alternately, a polymer or lower melting point metal may be melted in the proximal section of the tube, or certain thermosetting adhesives 56 including but not limited to cyanoacrylates, epoxies, polyesters or polyurethanes may be used to seal the internal cavity at its proximal end as depicted in FIG. 6D to form a non-hollow portion in the suture needle. An alternate method would combine both adhesive and mechanical attachment techniques wherein the suture is first dipped in adhesive and then inserted into the needle cavity and mechanically swaged in place.

The suture needles described herein may be produced from metal tubing made from surgical stainless steels commonly employed in the manufacture of suture needles, such as 420, 455, 4310, 302 or the group of high strength steels classified as maraging, using known needle making procedures such as grinding, coining, stamping, and drilling Needle blanks compatible with the needle making equipment of choice may be formed from a spool of metal tubing. Several different forming processes may be employed to produce these suture needles including: rotary swaging of the needle blank tip to reduce the cross-sectional area of the tubing, grinding on the top face of the swaged needle blank, swaging of the needle blank tip to form the needle tip shape, grinding to further refine the needle tip, stamping to from the shape of the body and create ribs, swaging on the proximal end of the needle to seal the cavity, forming of a channel for suture attachment, drilling of the needle for suture attachment, electropolishing to finish and clean the needle point and siliconizing to impart lubricity to the needle. The sequence of events in which these forming events occur may be varied. Moreover, the degree of constriction of the internal cavity near the distal end of the needle may be varied by adjusting one or more steps of the forming processes. Other processing techniques may be employed to produce these suture needles, including: laminating, forming and sectioning of metal sheets. However, forming of metal tubing is well suited to the equipment currently employed by many commercial manufacturers of suture needles.

Most commercially available suture needle/suture assemblies are made such that the needle shank has a hollow bore at one end, where the axis of the bore is parallel to the axis of the needle. A suture is assembled to such a needle by having one end inserted into the needle bore and secured therein by adhesive, or by deforming the needle at the bore to clamp the suture end in place. Therefore, the outer diameter of the suture needle is typically greater than, and preferably equal to, the outer diameter of the suture to be used in a particular surgical procedure. However, the outer diameter of the suture needle may be greater than the outer diameter of a first portion of the suture beginning at the distal end of the suture, but less than or equal to the outer diameter of the remainder of the suture.

Suture needles must withstand the forces imparted on them as they are driven through tissues. By incorporating an internal cavity into the suture needle, strength of the needle may be reduced. Elastic beam theory may be used to approximate the yielding moment of a straight needle under an applied bending force.

Yielding Moment=(Yield strength*Moment of Inertia)/Distance from neutral axis to needle surface.

Figure 7:
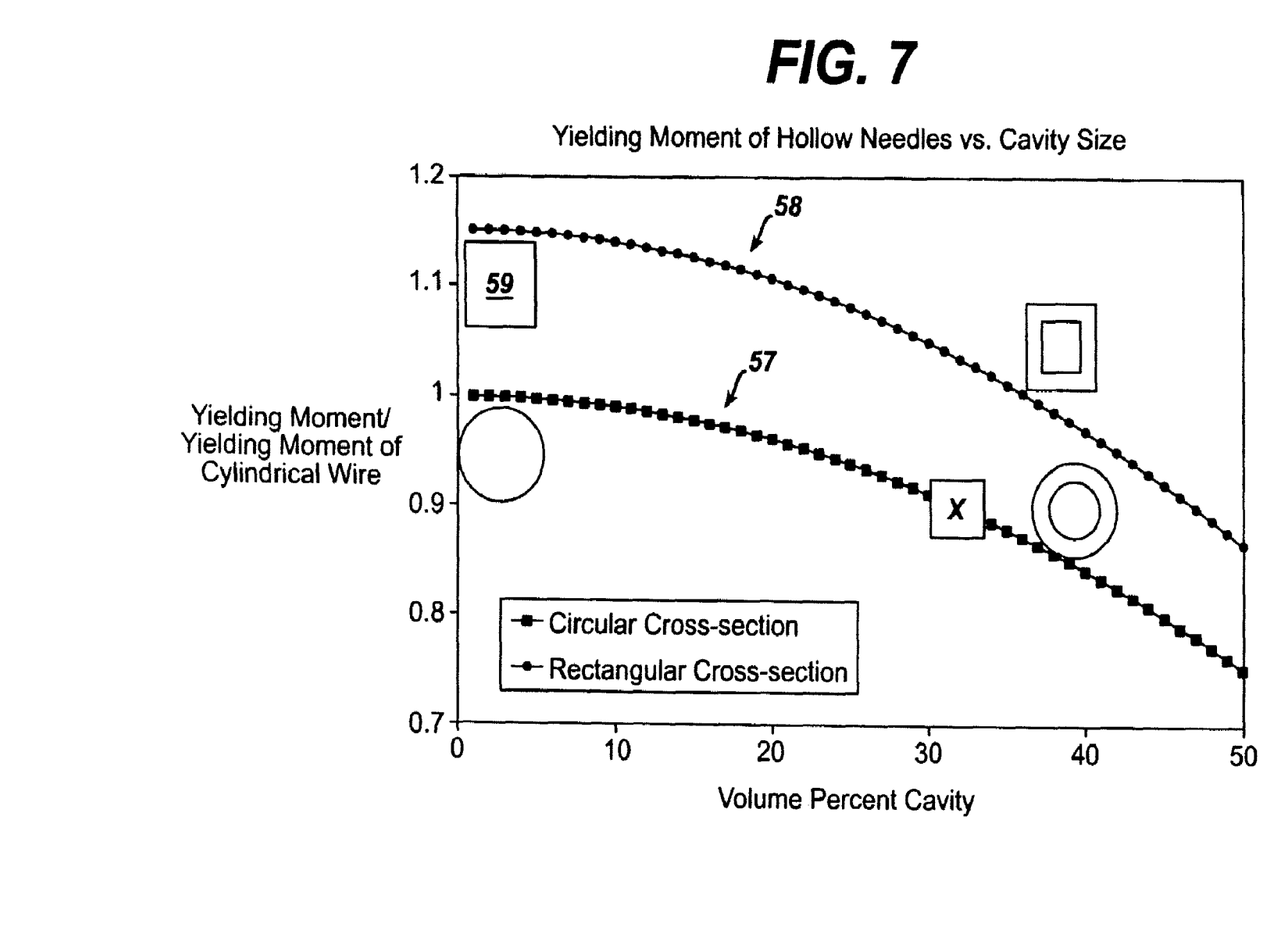
FIG. 7 shows the estimated relationship between the yielding moment of the suture needle and the size of the internal cavity for alternate needle body designs.

Both the moment of inertia and the distance from the neutral axis of the needle are affected by the cross-sectional shape of the needle. FIG. 7 shows the decrease in yielding moment that may occur for needles exhibiting circular 57 and rectangular 58 needle body cross-sections as the internal cavity in the needle becomes progressively larger. It is important to note that the relationship between cross-sectional area of the cavity and the yielding moment of the needle is not linear. Indeed, a cavity that comprises 30 percent of the cross-sectional area of the needle will lower the yielding moment of the needle by only approximately 10%, as shown by the designation X in FIG. 7. Furthermore, the yielding moment of a suture needle may be increased above the yielding moment of a cylindrical wire by producing a needle body with a rectangular cross-section 59. As indicated by FIG. 7, a hollow suture needle with a rectangular cross-section can be made to exhibit a higher yielding moment than a solid needle of equivalent bulk area with a circular cross-section. Consequently, it may be concluded that the suture needles of the invention may be designed to satisfy strength performance requirements in most applications.

The suture needle of the invention may be filled with a therapeutic or bioactive agent or fluid in a variety of ways. For example, a simple method for filling the internal cavity in the suture needle shown in FIG. 1, or the internal cavity of the suture needle assembly or suture needle/suture assemblies shown in FIG. 2, utilizes a short segment of elastomeric tubing, produced separately from the aforementioned devices, that is sealed on one end and open on the other. The short segment of elastomeric tubing may be filled with a fluid and then pressed over the distal end of the suture needle, forming a liquid tight seal between the short segment of elastomeric tubing and the needle body. The short segment of elastomeric tubing may then be compressed to force the fluid into the internal cavity of the suture needle or the internal cavity of the suture needle assemblies under pressure. The short segment of elastomeric tubing is then sealed with heat, RF, or ultrasound energy to complete the loading process. Alternatively, a thin metal band may be placed around the short segment of elastomeric tubing. After the short segment of elastomeric tubing is placed over the needle tip, the metal band is flattened to fill the internal cavity with the fluid under pressure. In both of the aforementioned embodiments the short segment of elastomeric tubing serves the dual functions of pressurizing device and needle cap or stopper used to retain the fluid in the needle under pressure. Other fluid loading devices that may be employed on a manufacturing setting include: pressure chambers and bench top servo-hydraulic devices. The fluid emitting suture needle that is connected to a reservoir 39 through the fluid conducting suture 35 shown in FIG. 3 may be loaded with a therapeutic or bioactive agent or fluid in a different way. An elastomeric tube serving as an inflatable connector may be attached to a reservoir such as a hypodermic needle or syringe on one end and to the proximal end of the fluid conducting suture 35 on the other. This elastomeric tube may then be inflated with the therapeutic fluid and sealed at its proximal end with a clamp to eliminate the need to continually supply pressure through the hypodermic needle or syringe. Since the opening in the suture needle and elastomertic tube attached to the proximal end of the suture are in fluid communication, the flow of fluid through the opening occurs immediately subsequent to the inflation of the elastomeric tube.

Figure 8:
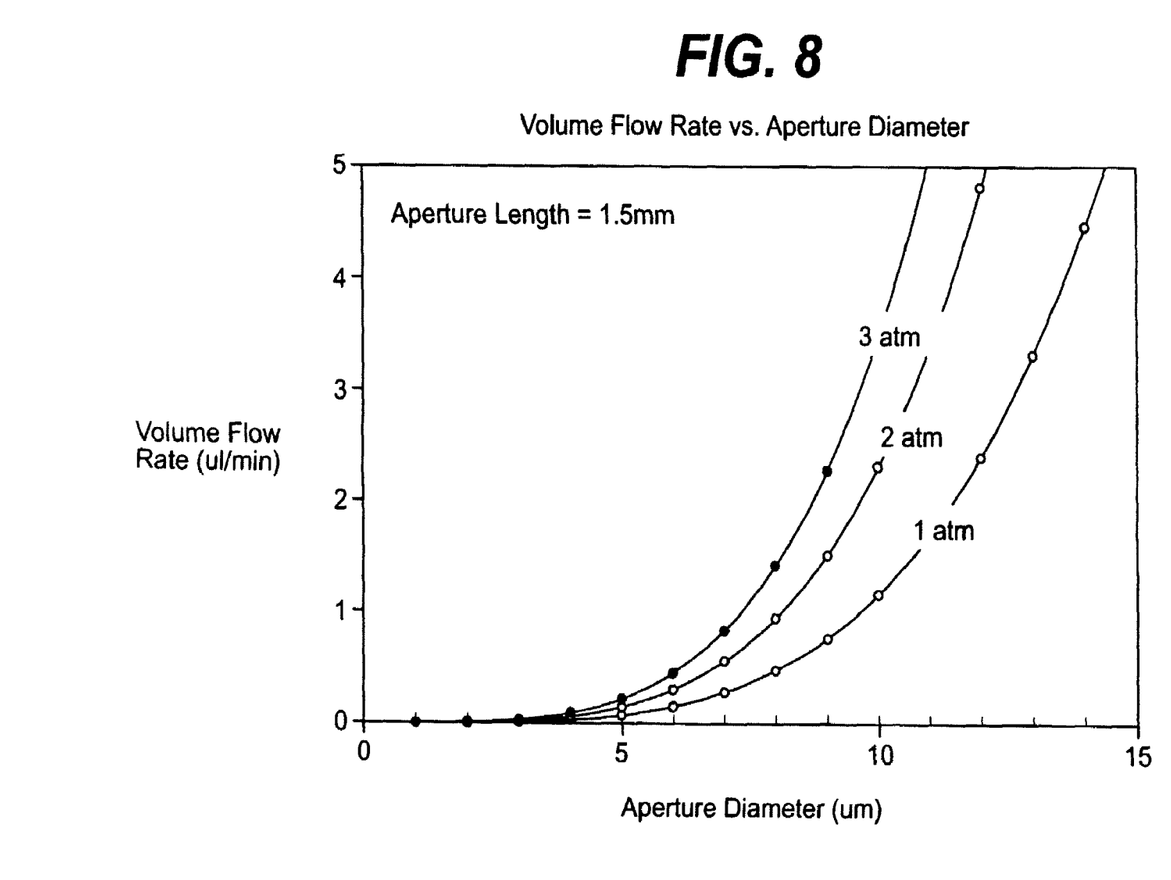
FIG. 8 shows the relationship between volume flow rate and aperture diameter as a function of gas pressure contained within the needle.

Sutures that may be used in conjunction with the suture needles shown in FIGS. 1 and 2A may be any conventional suture, including but not limited to non-absorbable monofilaments produced from polypropylene, nylon, polytetraflouroethylene (PTFE), and, bioresorbable monofilaments produced from polycaprolactone or catgut, non absorbable multifilament braids produced from polyethyleneterephthalate (PET), silk filaments, polypropylene, and absorbable multifilaments produced from polyglycolic-polylactic copolymers. Sutures that may be used in FIGS. 2B and 4A include but are not limited to absorbable and non-absorbable monofilament sutures. Sutures that may be used in FIGS. 2C, 2D, 4B, 4C and 4D include but are not limited to braided absorbable and braided non-absorbable sutures The rate at which the fluid is emitted from the suture needle is controlled predominantly be three factors: fluid viscosity, pressure, and needle aperture design. The Hagen-Poiseuille relationship for fluid flow through a pipe may be used to approximate the volume flow rate of the fluid through the needle.

$$\text{Volume Flow Rate} = (\pi * \text{Applied Pressure} * \text{Capillary Radius})/(8 * \text{fluid viscosity} * \text{capillary length})$$

where, applied pressure is the pressure exerted by the trapped gas or elastomeric reservoir attached to the proximal end of the suture, capillary radius is the effective diameter of the tube or orifice through which the fluid passes, and the capillary length is the effective length of the tube or cavity cross-section. Since the resistance to fluid flow through the aperture at or adjacent to the distal end of the suture needle is typically much greater than the resistance to fluid flow through the larger internal cavity of the suture needle of the embodiments shown in FIGS. 1 and 2, values for the radius and length of the aperture may be used to estimate fluid flow rate via the Hagen-Poiseuille relationship. FIG. 8 provides an example calculation of fluid flow rate as a function of the effective aperture diameter and pressure for a fluid with a viscosity equivalent to water.

Figure 9A:
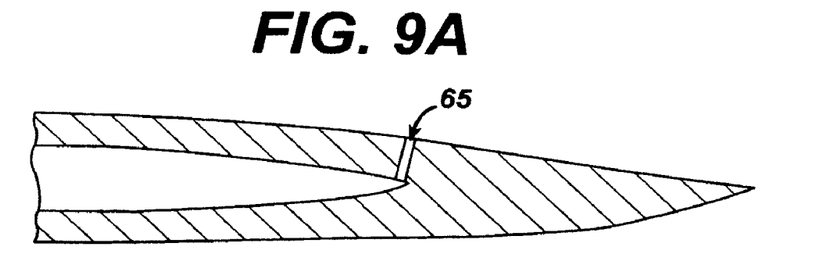
FIGS. 9A, 9B, 9C, 9D, 9E and 9F are schematic views of the needle tip having various aperture configurations.
Figure 9B:
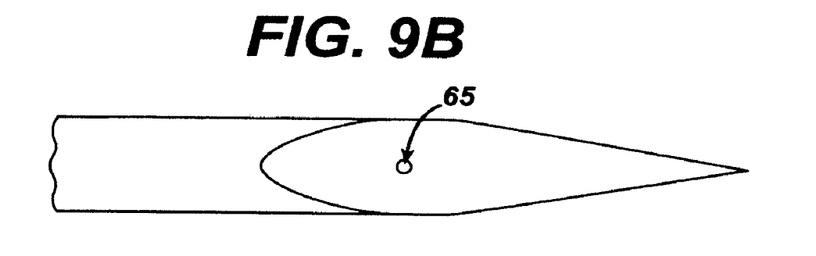
Figure 9C:
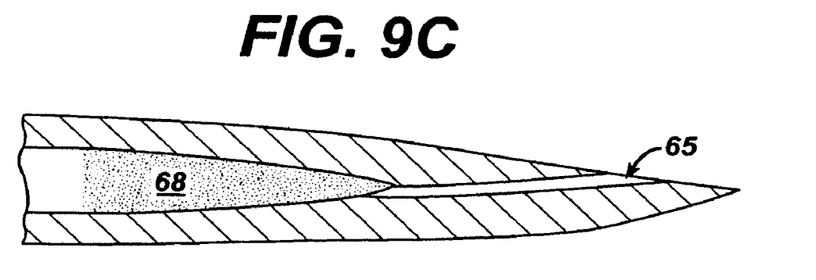
Figure 9D:
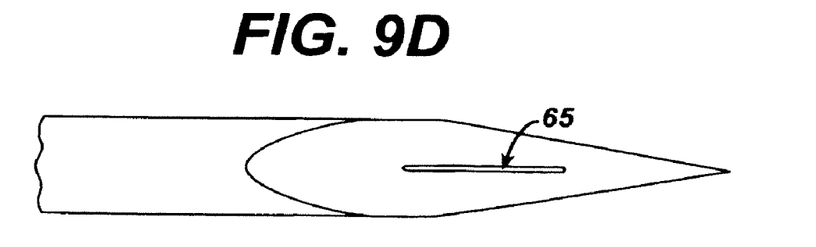
Figure 9E:
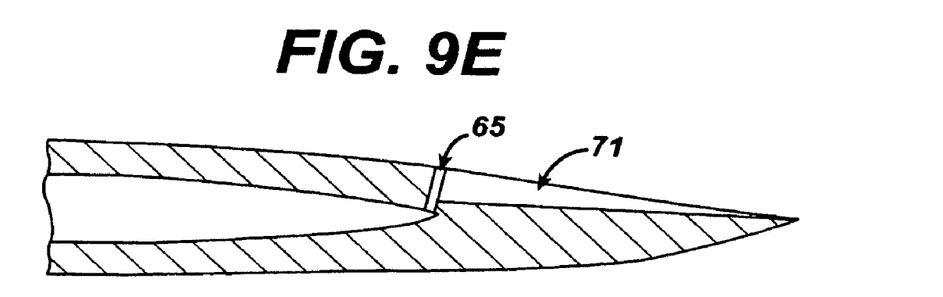
Figure 9F:
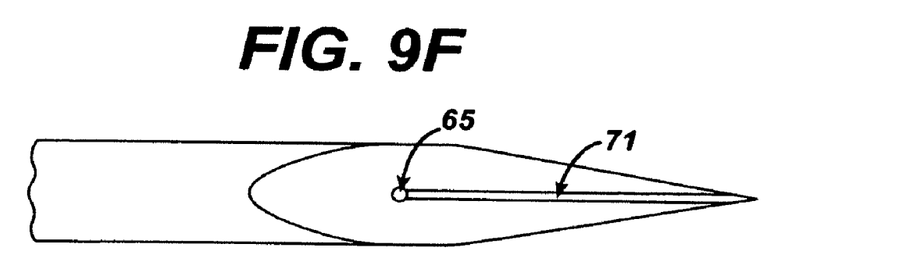

The fluid flow rate may be regulated by controlling the effective cross-sectional area of the aperture at or adjacent to the distal end of the suture needle. Several methods may be employed to regulate the aperture dimensions. The simplest method of regulating aperture size is by partially closing the internal cavity in the needle forming process. The point of the needle is formed by using a series of swaging operations that compress the tube walls together. The extent of each swaging operation may be varied to control the ultimate cross-sectional area of the aperture. Alternatively, a fine hole 65 may be laser drilled in the needle tip to precisely control volume flow rate as shown in the cross-sectional and top views on the needle tip in FIGS. 9A and 9B. Other methods such as the incorporation of porous or fibrous materials 68 into the needle tip, including but not limited to: polymeric, metal, or ceramic powders or fibers, as shown in cross-sectional and top views of the needle tip in FIGS. 9C and 9D, may be used to regulate the volume flow rate through the aperture as well. The fluid will be expelled from the needle tip where the aperture intersects with the surface of the needle tip. In most cases the aperture will not coincide with the point of the needle. This is indeed desirable to avoid clogging of the aperture. In many cases, the fact that the aperture is offset from the needle point may have no impact on the efficacy of the drug being deployed. However, in certain applications, such as the use of an antiviral agent to reduce the risk associated with accidental needle sticks, the suture needle may be most efficacious when the fluid wets out the very point of the needle. The use of low surface tension fluids may facilitate the wet-out of the needle point. Another option is to employ a needle tip that exhibits a depression or fine channel 71 extending from the aperture to the point of the needle, as shown in the cross-sectional and side views of FIG. 9E and FIG. 9F. The channel acts to transport the fluid directly to the needle point.

In the embodiments shown in FIGS. 1 and 2, it is important to note that since there is a finite molar quantity of gas trapped inside of the internal cavity of the suture needle, as the fluid is emitted from the suture needle the volume of the compressed gas increases, and according to the theory of gasses, the pressure exerted by the gas decreases. Since pressure influences the flow rate of the fluid through the needle, the flow rate slows at the pressure drops. In many applications, the fluid may provide a therapeutic effect despite the decrease in flow rate. If a near constant delivery rate is essential to the efficacy of a given fluid, a series of flow constrictors, similar in design to the contriction employed at the distal end of the suture needle may be formed along the length of the internal cavity of the suture needle. As the fluid passes each internal flow constrictor, it speeds up to counteract the decreasing pressure provided by the gas. Alternatively, the internal cavity may be filled with a porous material in such a way that the resistance to flow that occurs as the fluid passes through the porous media counteracts the decreasing pressure.

For the embodiment that employs a fluid conducting suture and reservoir, shown in FIG. 3, the aperture at or in the proximity of the distal end of the needle may be made large enough to provide minimal resistance to fluid flow. In this case the radius of the lumen inside the fluid conducting suture 36 and the overall length of the suture are the critical input values to the Hagen-Poiseuille relationship for calculating fluid delivery rate. A distinct advantage of this embodiment lies in the fact that if the reservoir is large in comparison to the volume of fluid being emitted during the wound closure procedure then a near constant delivery rate will be maintained.

Fluids that may be utilized with any of the suture needles described above include any therapeutic or bioactive agent or fluid, including but not limited to antimicrobial agents such as 2,4,4'-trichloro-2'hydroxydiphenyl ether, benzalkonium chloride, silver sulfadiazine, povidone iodine, triclosan, gentamiacin; anti-inflammatory agents, steroidal or non-steroidal, such as celecoxib, rofecoxib, aspirin, salicylic acid, acetominophen, indomethicin, sulindac, tolmetin, ketorolac, mefanamic acid, ibuprofen, naproxen, phenylbutazone, sulfinpyrazone, apazone, piroxicam, anesthetic agents such as channel blocking agents, lidocaine, bupivacaine, mepivacaine, procaine, chloroprocaine, ropivacaine, tetracaine, prilocaine, levobupivicaine, and combinations of local anesthetics with epinephrine etc., anti-proliferatives such as rapamycin, growth factors such as PGDF, scar treatment agents such as hylauronic acid, angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, prometbazin, meclizine, terfenadine, astemizole, fexofenidine, loratidine, aurothioglucose, auranofin, Cortisol (hydrocortisone), cortisone, fludrocortisone, prednisone, prednisolone, 6α-methylprednisone, triamcinolone, betamethasone, and dexamethasone; hemostatic agents such as thrombin, tranexamic acid, epinephrine; as well as antiviral and antithrombotic agents.

EXAMPLE

Figure 10A:
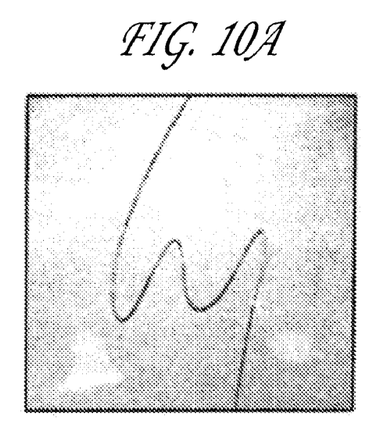
FIGS. 10A, 10B, 10C, 10D, 10E and 10F are images of bacterial colonies in agar culture with and without the delivery of an antimicrobial agent from the suture needle.
Figure 10B:
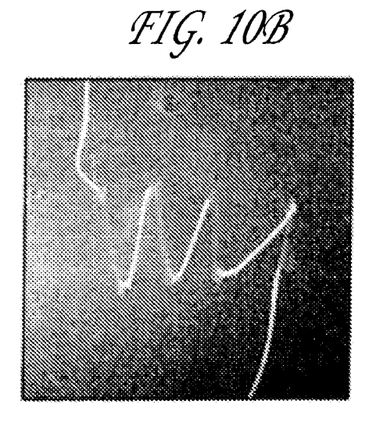
Figure 10C:
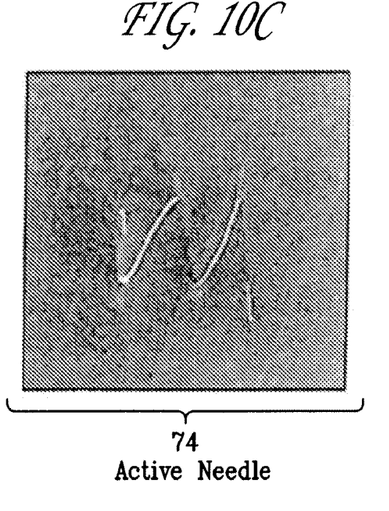
Figure 10D:
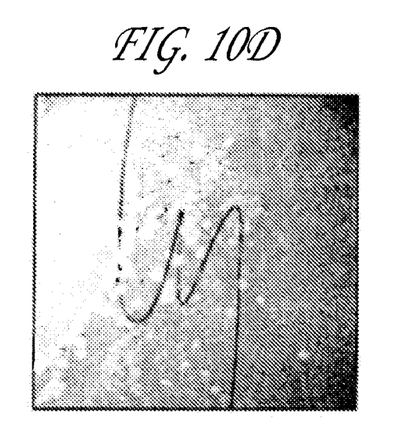
Figure 10E:
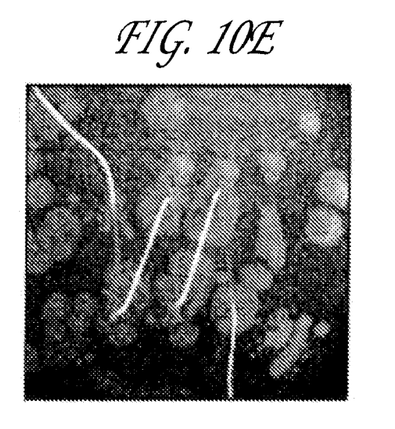
Figure 10F:
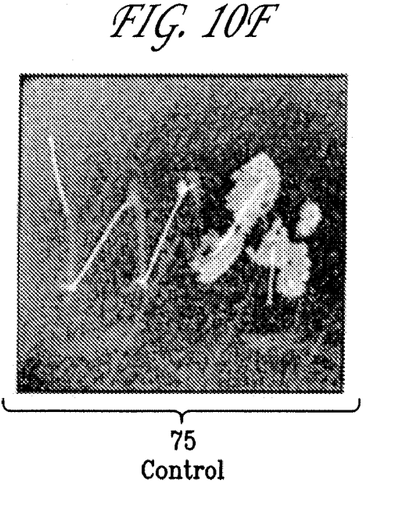

In vitro trials were conducted to evaluate the therapeutic efficacy of delivering an antimicrobial agent from the suture needle described in FIG. 1. Fluid emitting suture needles with a nominal outside diameter of 0.032" and an inside diameter of 0.019" were filled with a Triclosan bearing solution and pressurized to 2 atmospheres pressure. The liquid vehicle was a mixture of 75% propylene glycol and 25% Ethanol. Triclosan was added at a concentration of 0.1 g/ml solution. The total volume of fluid contained within the needle was ~3 microliters. A control set of needles that were not loaded with an active agent were produced as well for comparison. Multifilament PET sutures and monofilament polypropylene sutures were attached to the needles. Devices were activated by removing the cap 18 shown in FIG. 1 and passed through agar plates containing various bacteria commonly found in surgical site infections, including: *Staphylococcus Aureus, Escherichia. Coli* and *Enterococcus Facili*. A running stitch was performed with the fluid emitting suture needles as shown in FIGS. 10A, 10B and 10C, and with the control needles in FIGS. 10D, 10E and 10F, using approximately 3 to 4 passes with the entire procedure taking approximately 2 minutes. The bacteria were incubated for up to 1 week at 98.6 degrees Fahrenheit. In every case, a zone of inhibition where the bacteria colonies were unable to grow 74 was detected around the sutures that employed the fluid emitting suture needle, whereas the control groups that did not use a fluid emitting needle 75 did not impede bacterial colonization. Specifically, the bacteria used in FIGS. 10A and 10D was *Staphylococcus Aureus;* in FIGS. 10B and 10E, *Escherichia. Coli;* and in FIGS. 10C and 10F, *Enterococcus Facili*.

What is claimed:

1. A metal suture needle having a yielding moment and an internal cavity therein comprising:

a proximal end, a distal end, a point on the distal end, an opening at or in the proximity of the distal end, and a non-hollow portion or seal at or adjacent to the proximal end; the internal cavity having a cross-sectional area and being in fluid communication with said opening at one end and terminates at said non-hollow portion or seal at the other end;

a fluid residing within the internal cavity; and a compressed gas residing between the fluid and the non-hollow portion or seal, wherein the suture needle having a non-linear relationship between the cross-sectional area of the internal cavity and the yielding moment wherein the proximal end of the suture needle is attached to a suture.

2. The suture needle of claim 1, wherein the fluid is selected from the group consisting of antimicrobial agents, antibiodic agents, antiviral, antithrombotic, anti-inflammatory agents, anesthetic agents, anti-proliferatives, growth factors, hemostatic agents, sealants, adhesives, scar treatment agents, angio-genesis promoting agents, pro-coagulation factors, anti-coagulation factors, chemotactic agents, agents to promote apoptosis, immunomodulators, mitogenic agents, epinephrine, thrombin, tranexamic acid, triclosan, gentamiacin, diphenhydramine, chlorpheniramine, pyrilamine, promethazin, meclizine, terfenadine, astemizole, fexofenidine, loratidine, aurothioglucose, auranofin, Cortisol (hydrocortisone), cortisone, fludrocortisone, prednisone, prednisolone, 6a-methylprednisone, triamcinolone, betamethasone, and dexamethasone.

* * * * *